United States Patent [19]

Opitz

[11] 4,159,320
[45] Jun. 26, 1979

[54] ACTIVATED MASF

[75] Inventor: Hans-Georg Opitz, Wuppertal, Fed. Rep. of Germany

[73] Assignee: Bayer Aktiengesellschaft, Leverkusen, Fed. Rep. of Germany

[21] Appl. No.: 876,806

[22] Filed: Feb. 10, 1978

[30] Foreign Application Priority Data

Mar. 1, 1977 [DE] Fed. Rep. of Germany ....... 2708780

[51] Int. Cl.² .................... A61K 35/14; A61K 35/16; A61K 39/00
[52] U.S. Cl. ....................................... 424/101; 424/85
[58] Field of Search ........................... 424/101, 88, 85; 195/1.8

[56] References Cited

PUBLICATIONS

Pilet et al.–Chem. Abst., vol. 72, (1970), 98568a.

*Primary Examiner*—Sam Rosen
*Attorney, Agent, or Firm*—Sprung, Felfe, Horn, Lynch & Kramer

[57] ABSTRACT

The invention concerns MASF (mercapto-activatable serum factor) activated by a mercapto compound. Also included in the invention are processes for the preparation of said activated MASF, compositions containing said activated MASF and methods for the use of said activated MASF.

27 Claims, No Drawings

ACTIVATED MASF

The present invention relates to new formulations comprising activated MASF (mercapto-activatable serum factor), the immunoregulatory factor activated by mercapto compounds, processes for their preparation from human and/or non-human mammalian blood serum and their use in medicine, for example as medicaments or medicinal auxiliaries, such as diagnostic agents and reagents.

It has already been disclosed that 2-mercaptoethanol (formula: $CH_2SH\text{-}CH_2OH$) favourably influences the growth of lymphocytes in vitro (Broome, J. D., and M. W. Jeng, J. Exp. Med. 138:574 (1973) and Click, R. E., L. Benck and B. J. Alter. Cell Immunol. 3:156 (1972)). The action of 2-mercaptoethanol in an in vitro system which is able to synthesize antibodies has been thoroughly investigated (Mishell, R., and R. W. Dutton, J. Exp. Med. 126:423 (1967)). This system (Mishell-Dutton system) consists of a suspension of murine splenocytes. Together with foetal calf serum and an antigen, they can form, within 5 days, specific antibodies against the antigen administered. The synthesis of antibodies in this system essentially depends on the quality of the foetal calf serum used. It cannot be replaced by other sera; even a homologous serum, that is to say murine serum, has proved unusable. Meanwhile, even of the foetal calf sera, only selected so-called "good sera" make possible an immune response in the splenocyte suspensions. The addition of 2-mercaptoethanol to this system raises the number of surviving cells and decisively increases the synthesis of antibodies.

It has been demonstrated that the synthesis of antibodies depends on 3 types of cell, the T-lymphocytes and B-lymphocytes and the macrophages (Miller, J. F. A. P. and Mitchell, G. F. 1969, Transplant Rev. 1:3). If the macrophages are removed from the in vitro system, the system is no longer able to form antibodies (Shortman, K. and J. Palmer, Cell. Immunol. 2:399, (1971)). Some time ago it was shown that 2-mercaptoethanol is able to replace the macrophages completely in the synthesis of antibodies (Chen. Ch., and J. G. Hirsch, J. Exp. Med. 136:604 (1972)). All the other constituents of the system are however still necessary.

Investigations into the mechanism of the action of 2-mercaptoethanol showed that 2-mercaptoethanol, together with foetal calf serum, is able to greatly increase the DNA synthesis by T-lymphocytes (Lemke, H. and H. G. Opitz, J. Immunol. 117:388 (1976)). The observation that 2-mercaptoethanol stimulates the DNA synthesis of mixed lymphocyte cultures, without the addition of serum, (Katz-Heber, E., A. B. Peck, and R. E. Click, Eur. J. Immunol. 3:379 (1973)) led to the assumption that 2-mercaptoethanol acts directly on the lymphocytes, and that the serum present in the culture is able to increase the action of 2-mercaptoethanol in an unknown manner.

We have now discovered, surprisingly, that the action of certain mercapto compounds (as defined hereinbelow) preferably 2-mercaptoethanol compounds, on the synthesis of antibodies in vitro does not take place via a direct influence of the mercapto compound on lymphocytes. If foetal calf serum is incubated with the mercapto compound and the free mercapto compound is later removed by lyophilisation before the serum is added to the splenocyte cultures, it is found that, by preincubation with the mercapto compound, the serum has acquired the ability to replace macrophages completely in the synthesis of antibodies. Like, for example, 2-mercaptoethanol, a serum thus treated leads to a rise in the number of surviving cells and to an increase in the synthesis of antibodies. This observation proves that 2-mercaptoethanol is able to activate a serum component which was hitherto inactive. This serum factor which can be activated by 2-mercaptoethanol, is referred to hereinafter as MASF. This serum factor which can be activated by 2-mercaptoethanol, that is to say MASF, has a molecular weight in the order of magnitude of 50,000. The factor is present in varying concentrations in different foetal calf sera. Foetal calf sera with a high proportion of this factor are the most suitable for the synthesis of antibodies in vitro. "Unsuitable" foetal calf sera possess significantly less of MASF than do the so-called "good sera."

It is nevertheless also possible to isolate sufficient MASF from "unsuitable" sera by concentrating the factor. In general, in the case of sera other than foetal calf sera, the factor MASF cannot be detected in the untreated whole sera.

It has now been found that blood serum formulations of human or animal origin which contain the activated immunoregulatory factor MASF obtained by reaction of blood serum or blood serum fractions with a mercapto compound of the formula

wherein
R is hydrogen or methyl,
X is hydroxyl or amino and
Y is hydrogen, carboxyl or lower alkyl,
can be used for initiating and increasing the synthesis of antibodies and can be employed, for example, as medicaments or as medicinal auxiliaries, such as diagnostic agents and reagents.

Thus the present invention provides activated MASF comprising the factor MASF, as defined hereinbefore, activated by a mercapto compound of the formula

wherein
R is hydrogen or methyl,
X is hydroxyl or amino and
Y is hydrogen, carboxyl or alkyl having 1 to 6 carbon atoms and optionally substituted by hydroxyl and/or mercapto.

Furthermore, it has been found that the above mentioned blood serum formulations can be obtained in a simple manner by reacting blood serum or MASF-containing blood serum fractions with mercapto compounds of the formula (I) and optionally fractionating the treated blood serum or blood serum fractions e.g. by the use of biochemical fractionation methods.

Thus in a further aspect the present invention provides a process for the preparation of activated MASF comprising reaction of MASF, as defined hereinbefore, with at least one mercapto compound of the formula

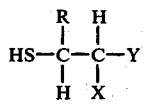

(I)

wherein
R is hydrogen or methyl,
X is hydroxyl or amino and
Y is hydrogen, carboxyl or alkyl having 1 to 6 carbon atoms and optionally substituted by hydroxyl and/or mercapto.

If whole foetal calf serum is used as the starting material for the preparation of the activated MASF-containing blood serum formulations, in principle, as already mentioned above, no fractionation (such as, for example, chromatography or fractional precipitation) is necessary, but this is usually desirable in order to concentrate the MASF and separate off concomitant substances.

In general, in the case of sera other than foetal calf serum, preparative fractionation is desirable for the preparation of the activated MASF containing blood serum formulations.

In certain cases, for example, in the case of murine serum, which contains inhibitory and cytotoxic substances fractionation will usually be necessary to remove these substances depending upon the intended use of the end product. In addition, it is usually necessary to achieve or exceed a certain MASF factor threshold concentration in order to achieve the desired immunological effect.

It is possible to determine the threshold concentration by determining the dose/activity relationship, for example using the above mentioned Mishell-Dutton method, and this determination should be carried out experimentally with each blood serum formulation.

Since in a heterologous system (using sera of other species) all high-molecular substances must be regarded as potential antigens, conclusions with respect to a particular antigen are only to be drawn with caution. It is therefore an important requirement that investigations of this type be carried out in a homologous system, that is to say the immunocompetent cells and supplementary serum must originate from the same species. This was not possible hitherto because of the above mentioned inhibitory and/or cytotoxic activity of such sera.

Active autologous formulations are obtained here in a surprisingly simple manner by separating off (for example by precipitation processes and/or chromatographic processes) the inhibitors and/or cytotoxic substances.

Possible fractionation methods, customary in biochemistry, for obtaining blood serum fractions containing MASF or activated MASF are preferably chromatographic and precipitation methods.

Examples of chromatographic fractionation methods which may be mentioned are: gel chromatography, for example using cross-linked dextrans of a suitable pore size (for example Sephadex ® G 100) or agarose formulations (for example Sepharose ®) or polyacrylamide gels (for example Biogel ® preferably of pore size P 60 or P 120), and ion exchange chromatography using, for example, columns of the following: DEAE-Sephadex ® (=a cross-linked polydextran containing diethylaminoethyl groups), SE-Sephadex ® (=a cross-linked polydextran containing sulphonylethyl groups) or ion exchangers based on polystyrene, for example Dowex ®.

Possible precipitants for carrying out precipitation methods are a number of different chemical substances, for example inorganic salts, such as ammonium sulphate, in aqueous solutions of various concentrations; other suitable precipitants being higher-molecular weight compounds, such as for example, polyethylene glycols with a preferred molecular weight range from 1,000 to 10,000, preferably from 3,000 to 5,000. Further precipitants are, for example, organic solvents, such as lower alcohols (for example ethanol) or ketones (for example acetone).

In addition, molecular filtration (ultrafiltration), for the purpose of excluding low-molecular weight material, is a fractionation method which may be used for obtaining blood serum fractions which contain MASF or activated MASF free from inhibitors.

The reaction with the mercapto compound of the general formula (I), which is required for obtaining the activated blood serum formulations, may be carried out at the start or at the end of a process for their preparation, or after any component step, for example, fractionation step of the preparative process.

The mercapto compound is usually added in a concentration of from 0.01 to 50 mM, preferably from 1 to 20 mM.

In the case of individual mercapto compounds (I), the following are examples of suitable ranges of concentrations which may be added:
ethanethiol: 5–10 mM
1-propanethiol: 2–10 mM
2-propanethiol: 1–10 mM
cysteamine: 1–10 mM
2-mercaptoethanol: 1–5 mM
3-mercaptopropionic acid: 1–10 mM
L-cysteine: 4–20 mM
thioglycerine: 0.01–10 mM
dithiothreitol: 2–10 mM 2-Mercaptoethanol (referred to hereinafter as mercaptoethanol) is in general most preferred and may be used in the case of all formulations.

As mentioned above, the activation of the MASF can take place at the start or at the end of the preparative process or after any fractionation step of the preparative process, but it preferably takes place at the start of the preparation process.

In the case of human blood serum, the following sequence of the steps has proved advantageous:

(1) Activation of the human blood serum with a mercapto compound of the formula (I), preferably with mercaptoethanol. For this, the serum may, for example, be incubated with $10^{-3}$ M 2-mercaptoethanol at a temperature of from 0° to 35° C., preferably at room temperature (20°–23° C.) for from 0.5 to 5, most preferably 1 to 2 hours.

(2) Molecular filtration of the activated human blood serum so as to exclude low-molecular and/or high-molecular weight material (for example using a Diaflo ultrafiltration membrane such as a PM 30 or XM 100 A membrane).

(3) Ammonium sulphate precipitation: activated MASF is present in the proteins which precipitate at from 35% to 55% $(NH_4)_2SO_4$ saturation.

(4) Polyethylene glycol fractionation: activated MASF is precipitated with a ten percent strength polyethylene glycol (PEG) solution. The PEG precipitation can be used in place of the ammonium sulphate precipitation or can follow the $(NH_4)_2SO_4$ precipitation as a further purification step.

(5) Fractionation of the resulting serum fraction containing activated MASF using Sephadex G 100. The exclusion chromatography can be repeated in order to obtain a better purification.

(6) Separation of the fraction containing activated MASF using an ion exchanger (for example Sephadex AD 50 DEAE).

It should however be noted here that it is not essential to carry out all of the above mentioned steps in order to obtain acceptable ready-to-use blood serum formulations and further preferred processes are illustrated in Examples A to H hereinbelow.

In principle, it is possible to lyophilise the solutions to concentrate the activated MASF and remove volatile mercaptans, such as, for example unreacted 2-mercaptoethanol, after any component step of the working up process. Other concentration processes for example precipitation with alcohols and/or ketones, for example ethanol or acetone, or concentration by molecular sieve filtration, may also be used.

In all the stages of the purification process for all the blood sera employed according to the invention (both human and non-human animal sera) the properties of the various fractions formed are desirably monitored preferably with the aid of the three following test systems:

1. Determination of the action of the formulation containing activated MASF on DNA synthesis in special $L_{1210}$ cells selected with regard to MASF factor activation (so-called $L_{1210}$-FiO30 cells).

2. Determination of the action of the formulations containing the activated MASF factor on DNA synthesis in T-lymphocyte cells (radioactive method of determination) (incorporation of 3H-thymidine) and 3. Determination of the action of the formulation containing the activated MASF factor on the synthesis of antibodies by splenocytes (Mishell-Dutton system).

The two test procedures 1. and 2. are briefly described below:

(1) Action of activated MASF on the growth of $L_{1210}$-FIO 30 cells.

The $L_{1210}$ cell line used according to the application requires activated MASF for its growth. This cell line is designated as a $L_{1210}$-FIO 30 cell line. Its growth rate, measured by the incorporation of 3H-thymidine (TdR) in DNA, depends on the quantity of activated MASF available. This cell line is thus suitable for the detection and standardisation of activated MASF.

$2 \times 10^4$ $L_{1210}$ cells are cultured for 24 hours with and without activated MASF. During the last 6 hours the cells receive $0.5\mu$ Ci of 3H-TdR. (micro-Curie)

(2) Stimulation of T-lymphocyte cells ("T cells").

T cells are isolated in accordance with the method described by Julius et al., Eur. J. Immunol. 3, 645 (1973). In each case $5 \times 10^5$ T cells are cultured with or without activated MASF. After 48 hours, all the cultures receive $1\mu$ Ci of 3H-thymidine. After a further 24 hours, the incorporation of 3H-thymidine into the DNA of the T cells is determined. Cells which multiply have a significantly increased DNA synthesis. Since activated MASF specifically causes the proliferation of T cells and this proliferation is characterised by an increased incorporation of 3H-thymidine, this test is also suitable for determining the activity of activated MASF.

For diagnostic purposes it is possible according to another aspect of the invention to determine T-cell responsiveness by using the same test system as described above provided that the MASF preparation is standardised. This can be performed with the aid of a diagnostic kit, similar or identical to that used for mitogenic stimulation of lymphocytes as described by W. I. Waithe and K. Hirschhorn in Handbook of Experimental Immunology, Volume 2, Chapter 25, (Blackwell Scientific Publications, London, 1973).

The activated MASF-containing formulations according to the invention have a pronounced immunoregulatory, in particular immunostimulating, action. They are particularly suitable for the treatment of disorders of the macrophage function and of the lymphocyte T cell function or for the treatment of induced immunodeficiencies, which occur, for example, after the administration of cytostatic medicines.

Furthermore, the activated MASF formulations according to the invention could be employed for the treatment of anergic conditions in particular in the case of tumour diseases.

In order to cure anergic conditions by polyclonal multiplication of T-lymphocytes, because of the nitrogenic action of the formulations according to the invention which has been detected, they can be employed for the treatment of induced anergic conditions, for example after the treatment of tumour diseases and chronic infectious diseases using cytotoxic substances.

The activated MASF-containing blood serum formulations according to the invention can be employed both in human medicine and in veterinary medicine.

The activated MASF according to the invention can be used therapeutically in a highly pure form or conveniently in the form of an enriched blood serum formulation. An advantage of formulations of this type is that the homologous factor can be prepared in a simple manner for each species of animal and each human patient under consideration.

When an activated MASF formulation according to the invention is used as a medicinal auxiliary, it is used, above all, as a diagnostic agent and as a reagent.

Insufficiencies in the immunoregulatory profactor can be diagnosed in a simple manner with the aid of the MASF formulations according to the invention.

Furthermore, the activated MASF formulations according to the invention can be employed as reagents for the study of lymphocytes. Since it is possible, as mentioned above, to work in a homologous system, the formulations according to the invention are also suitable for the investigation of human lymphocytes.

As stated above, the invention also relates to the use in human and veterinary medicine of the compounds of the invention.

The present invention provides a pharmaceutical composition containing as active ingredient activated MASF of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or isotonic aqueous solution.

The invention also provides a medicament in dosage unit form comprising activated MASF.

The invention also provides a medicament in the form of ampoules activated MASF (mercapto-activatable serum factor).

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

For parenteral administration, solutions and emulsions should as far as possible be sterile, and, if appropriate, blood-isotonic.

In addition to a compound of the invention, the pharmaceutical compositions and medicaments according to the invention can also contain other pharmaceutically active compounds. They may also contain a plurality of activated MASFs.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape of packaging, for parenteral administration and will usually be in the form of ampoules.

The production of the above mentioned pharmaceutical compositions and medicaments is carried out by any method known in the art, for example, by mixing the active ingredient(s) with the diluent(s) to form a pharmaceutical composition (e.g. a solution for injection) and then forming the composition into the medicament (e.g. ampoule).

This invention further provides a method of combating (including prevention, relief and cure of) the above-mentioned diseases in warm-blooded animals, which comprises administering to the animals an activated MASF of the invention alone or in admixture with a diluent or in the form of a medicament according to the invention.

It is envisaged that these active compounds will be administered parenterally (for example intra-muscularly, subcutaneously, intraperitoneally or intravenously), preferably intravenously. Preferred pharmaceutical compositions and medicaments are therefore those adapted for intravenous administration, such as injection solutions or suspensions. Administration in the method of the invention is preferably intravenously.

The dosage must usually be determined individually, according to the intended use and aim thereof and the nature of the formulation, and with the aid of standardisation tests and standard formulations.

The standardisation and therefore dosage of the activated MASF factor is determined on an individual basis with the aid of the generally available leukemic cell line $L_{1210}$. This cell line exhibits an activated MASF-factor-dependent growth. A biological unit can be defined as the dose of activated MASF factor allowing 50 percent of the maximum, 3H-thymidine incorporation by $10^5$ $L_{1210}$ cells per milliliter.

On the basis of this unit of dosage 100–10,000, preferably 500–2000 units are required in general per kilgram bodyweight in order to obtain and immune stimulation.

The following examples of the preparation of activated MASF-containing blood serum formulations illustrate some preferred aspects of the invention.

EXAMPLE A

2-Mercaptoethanol was added to 20 ml of foetal calf serum to give a $10^{-3}$ molar solution. The solution was left to stand for two hours at 20° C. Ammonium sulphate precipitation (fractional precipitation) was then carried out and the fraction which precipitated at from 33 to 55% ammonium sulphate saturation was isolated.

Lyophilisation and exhaustive dialysis against physiological sodium chloride solution then followed.

The activated MASF-containing fraction obtained was tested in the biological systems described above ($L_{1210}$ cells FIO-30, DNA synthesis in T-lymphocytes and Mishell-Dutton system).

EXAMPLE B

2-Mercaptoethanol was added to 20 ml of foetal calf serum to give a $10^{-3}$ molar solution. The solution was left to stand for 3 hours at room temperature (22° C.).

Ammonium sulphate fractionation was then carried out, the fraction precipitating at between 33 and 55% ammonium sulphate saturation again being isolated.

The above mentioned ammonium sulphate precipitated fraction was fractionated using Sephadex ® G-100. A Tris-HCl buffer is used as the eluant (0.05 M Tris-HCl/0.1 M NaCl/pH 7.5).

(Sephadex ® G-75, Sephadex ® G 150, Sephacryl ® S-200 or Biogel ® can be used instead of the Sephadex ® G-100).

Lyophilisation of the activated MASF-containing fraction and subsequent extensive dialysis against physiological sodium chloride solution are then carried out.

The activated MASF-containing fraction was then tested as mentioned in Example A. The further sera which follow were also processed to give corresponding formulations in a manner analogous to the processes described above for foetal calf serum: human serum, murine serum, rat serum, rabbit serum and cattle serum.

EXAMPLE C

The preparation is carried out as described in Example B, with the difference that the serum factor MASF was not activated at the start of the preparation procedure but at the end, that is to say before the lyophilisation.

EXAMPLE D

2-Mercaptoethanol is added to 50 ml of human serum to give a $10^{-3}$ molar solution and the solution is left to stand for 2.5 hours at 20° C.

Ammonium sulphate precipitation was then carried out and the fraction which precipitates at from 33 to 55% ammonium sulphate saturation was isolated. A second precipitation with 40 percent strength ethanol at 4° C. then followed. The fraction was then further fractionated using Sephadex ® G 100 using as eluant 0.05 M Tris-HCl/0.1 M NaCl (pH 7.5).

A further fractionation was carried out using the ion exchanger DEAE-Sephadex ® A 50 (eluant: 0.05 M Tris-HCl, pH 7.5). Lyophilisation and extensive dialysis against physiological sodium chloride solution were then carried out. Finally, the biological tests mentioned in Example A were again carried out.

EXAMPLE E

The preparation was carried out analogously to method D, with the difference that the activation process with 2-mercaptoethanol was only carried out after the ion exchange step (using DEAE-Sephadex ®).

EXAMPLE F

2-Mercaptoethanol was added to 50 ml of murine serum (or rabbit serum) to give a $10^{-3}$ molar solution (temperature 20° C., activation time: two hours). The serum proteins were then precipitated by contacting with a 10 percent strength polyethylene glycol solution (molecular weight about 4,000) for 4 hours at 20° C. Molecular filtration was then carried out using an Amicon XM 100 A filter. Fractionation of the protein fraction using Sephadex ® G 100 and further fractionation using the ion exchanger DEAE-Sephadex A 50 were then carried out. The fraction was then subjected to lyophilisation and extensive dialysis against physiological sodium chloride solution.

Finally, the biological tests were carried out as mentioned in Example A.

EXAMPLE G

The preparation was carried out analogously to method F, with the difference that the activation process was only carried out after the fractionation using the DEAE-Sephadex ion exchanger ($10^{-3}$ M 2-mercaptoethanol, 2 hours at 20° C.).

EXAMPLE H

2-Mercaptoethanol was added to 50 ml of human serum to give a $10^{-3}$ molar solution and the solution was left to stand for 3 hours at room temperature (22.5° C.). A molecular filtration by means of an Amicon XM 100 A filter was carried out in order to exclude high-molecular weight constituents. A further molecular filtration by means of an Amicon PM 30 filter was carried out in order to exclude low-molecular weight constituents.

Finally, biological tests were carried out as described in Example A.

EXAMPLE 1

Action of the immunoregulatory activated factor MASF on the synthesis of antibodies in vitro.

The action of the activated factor MASF on the synthesis of antibodies can be shown in vitro in a simple manner. Murine splenocyte cultures which contained all the cell species necessary for the synthesis of antibodies (T-lymphocytes, B-lymphocytes and macrophages), and those from which the macrophages had been removed were incubated with blood serum preparations which on the one hand contained the factor MASF activated with 2-mercaptoethanol and on the other hand contained the non-activated factor MASF. Sheep erythrocytes were added to all the cultures as an antigen. The formation of antibodies was measured after culturing for five days; for the results see Table 1. The results given show that the factor is able to replace the function of the macrophages in the synthesis of antibodies. The formation of antibodies was detected by measuring the synthesis of "19 S antibodies." The number, per culture, of cells forming antibodies is indicated in Table 1 (Plaque-forming cells ("PFC")/culture). The 19 S antibodies are antibodies of the IgM type. (The test method is described by Mishell and Dutton, J. Exp. Med. 126: 423 (1967)).

The macrophages were removed from the splenocyte suspension in accordance with the method of Lundgren et al, Clin. Exp. Immunol. 3, 817 (1968).

Table 1

| Cell system used | Blood serum formulation containing the factor MASF | Synthesis of 19 S antibodies (PFC/culture) |
|---|---|---|
| Murine splenocytes | activated (prepared according to Example A) | 5,260 |
| Murine splenocytes | not activated (that is to say Example A without the addition of mercaptoethanol) | 3,970 |
| Splenocytes free from macrophages | activated (prepared according to Example A) | 4,950 |
| Splenocytes free from macrophages | not activated (that is to say Example A without the addition of 2-mercaptoethanol) | <100 |

EXAMPLE 2

Replacement of the serum by the activated factor MASF.

Foetal calf serum is absolutely necessary in the customary systems known hitherto which synthesise antibodies in vitro. The results summarised in Table 2 show the action on the synthesis of antibodies by normal splenocytes (containing, inter alia, T-lymphocytes and B-lymphocytes and macrophages) and by macrophage-free splenocytes of mice by blood serum formulations which contain the factor activated with mercapto compounds, with and without the addition of foetal calf serum. The results show that activated MASF by itself is able to make the synthesis of antibodies possible and thus to replace entirely the other components foetal calf serum. The synthesis of antibodies is again measured by the formation of 19 S antibodies, analogously to the method given for Table 1.

The formation of 19 S antibodies is given in Table 3, again analogously to Tables 1 and 2, as a measure of the immune response.

Table 3

| Addition of different doses (indicated in percent) of a blood serum formulation which contains the mercapto-ethanol-activated MASF factor (prepared according to Example B) | Synthesis of 19 S antibodies (PFC/culture) | | |
|---|---|---|---|
| | Foetal Calf serum I | Foetal calf serum II | Foetal calf serum III |
| 5% | 4,350 | 1.740 | <100 |
| 10% | 9,050 | 4,400 | <100 |
| 20% | 10,070 | 9,700 | 2,030 |
| 30% | 10,000 | 9,400 | 4,650 |
| 40% | — | 10,100 | 8,050 |
| 50% | — | — | 8,620 |
| 0 (control | <100 | <100 | <100 |

EXAMPLE 4

Action of activated MASF on the growth of cell line $L_{1210}$ FIO30.

As a rule, permanent cell lines of lymphoid origin require foetal calf serum for their growth. Table 4 shows that the above mentioned cell line only requires the 2-mercaptoethanol-activated factor.

It is thus possible to replace the otherwise customary foetal calf serum by the activated MASF factor. This fact has great advantages with respect to the standardisation of the growth of cell lines.

Table 4

| Permanent cell lines of lymphoid origin receive | DNA synthesis/ 30 cells/incorporation of 3H-thymidine (cpm) |
|---|---|
| (a) — | 270 |
| (b) Foetal calf serum reacted with mercaptoethanol | 12,300 |
| (c) A blood serum formulation which contains the mercaptoethanol-activated factor MASF (prepared according to Example A) | 14,600 |
| (d) A blood serum formulation which contains the non-activated factor (analogous to Example 1, but without activation with mercaptoethanol) | 320 |
| (e) A blood serum formulation from human serum (prepared according to Example D) | 9,770 |
| (f) A blood serum formulation from human serum/non-activated factor (analogous to Example D, but without activation with mercaptoethanol) | 110 |
| (g) Blood serum formulation from murine serum (prepared according to Example F) | 7,650 |
| (h) A blood serum formulation from murine serum/non-activated factor (analogous to Example F, but without activation with mercaptoethanol) | 80 |

*cpm = "counts per minute"

EXAMPLE 5

Detection of MASF factor in different sera.

Foetal calf serum was hitherto the only serum which made the synthesis of antibodies by splenocytes in vitro possible. Since the 2-mercaptoethanol-activated factor MASF of foetal calf serum is the only substance therein necessary for the synthesis of antibodies, the most diverse sera were investigated to discover if they contain this factor, and if so, in what concentration. As Table 5 shows, the MASF factor was found in all the sera investigated.

Table 5

| Isolation of fractions which contain the mercaptoethanol-activated factor MASF (according to Example B) from the serum of | Synthesis of 19 S antibodies, PFC/ culture |
|---|---|
| Mouse | 7,360 |
| Rat | 5,240 |
| Rabbit | 8,130 |
| Cattle | 4,280 |
| Human | 9,420 |

EXAMPLE 6

Stimulation by MASF of the DNA synthesis in T cells.

The addition of activated MASF factor to splenocyte cultures significantly increases the DNA synthesis in these cultures.

Table 6 shows that the activated MASF factor specifically stimulates DNA synthesis in T cells. The extent of the DNA synthesis in T cells depends on the quantity of activated MASF factor.

Table 6

| Lymphocyte population | DNA synthesis/$10^6$ cells (incorporation of $^3$H-thymidine, cpm) Factor dose used (foetal calf serum formulation according to Example B) | | | | |
|---|---|---|---|---|---|
| | 1% | 2.5% | 5% | 10% | 20% |
| Splenocytes | 200 | 1,700 | 5,000 | 7,600 | 6,300 |
| B-lymphocytes | 400 | 1,070 | 960 | 830 | 950 |
| T-lymphocytes | 420 | 2,640 | 4,210 | 10,130 | 9,460 |

EXAMPLE 7

In vivo activity of the activated factor MASF/rabbit experiment.

The action of the activated factor MASF on the synthesis of antibodies in vivo was investigated. Serum was removed from rabbits and one half of the serum was activated with mercaptoethanol whilst the other half was not activated. The factor was prepared according to Example F. Some of the animals were given their own factor administered in the activated form and the other half were administered the non-activated factor. Simultaneously with the administration of the factor, the rabbits were given cattle serum albumin (CSA) as an antigen. The titre of antibodies against cattle serum albumin was determined in the individual sera after fourteen days. It was shown that the rabbits treated with their own activated factor displayed a significantly higher synthesis of antibodies than the control animals. (For this, see the summary of the results in Table 7).

The titre of antibodies was determined immunoelectrophoretically.

Table 7

| Blood serum formulation used, which contains the factor MASF (rabbit formulation, prepared according to Example F) | Anti-CSA antibody |
|---|---|
| activated with mercaptoethanol | + + |
| not activated (analogous to Example F, but without reaction with mercaptoethanol) | — |
| controls | — |

The symbols here have the following meanings:
+ + = Antibodies of the IgG type
— = No formation of antibodies

EXAMPLE 8

In vivo activity of the activated factor MASF/mouse experiment.

The action of activated human factor MASF on the synthesis of antibodies in mice was investigated. Mice were given sheep erythrocytes as an antigen. Simultaneously, the animals were given mercaptoethanol-activated factor or non-activated factor. As the results show, the synthesis of antibodies against sheep erythrocytes is significantly increased in the animals which received the activated factor.

The results are summarised in Table 8. The number of cells forming antibodies (19 S antibodies)/$10^6$ splenocytes is given.

Table 8

| Test substance | Synthesis of 19 S antibodies PFC/$10^6$ spleno- cytes |
|---|---|
| Sodium chloride | 44 |

Table 8-continued

| Test substance | Synthesis of 19 S antibodies PFC/$10^6$ splenocytes |
|---|---|
| A blood serum fraction which contains the mercaptoethanol-activated factor MASF (human serum formulation according to Example E) | 754 |
| A blood serum fraction which contains the non-activated factor MASF (analogous to Example E, but without mercaptoethanol-activation) | 244 |

EXAMPLE 9

Action of the 2-mercaptoethanol-activated factor MASF on cellular immunity.

The activated factor MASF has an action on T lymphocytes. These cells are, above all, carriers of cellular immunity. Cellular immunity is usually measured in mixed lymphocyte cultures, that is to say lymphocytes of one donor are mixed with lymphocytes of another donor. One of the two lymphocyte populations is first irradiated, in order to exclude reactions of these cells. These cells serve as a stimulant. The irradiated allogenic lymphocytes are foreign to the untreated lymphocyte population and the latter reacts with increased DNA synthesis. The DNA synthesis is determined via the incorporation of $^3$H-thymidine. As Table 9 shows, mixed lymphocyte cultures display a significantly increased DNA synthesis, that is to say the cellular immunity is increased by MASF.

Table 9

| Composition pf the lymphocyte cultures | The lymphocyte cultures contain | Incorporation of $^3$H-thymidine in cpm (counts per minute) |
|---|---|---|
| AA$_x$ | A blood serum fraction which contains the factor MASF (prepared according to Example D) | 324 |
| AA$_x$ | Medium (RPMI-1640 medium) | 80 |
| AB$_x$ | A blood serum fraction which contains the factor MASF (prepared according to Example H) | 7,212 |
| AB$_x$ | Medium (RPMI-1640 | 1,565 |
| Lokucine | 50 | 50 |

A$_x$ or B$_x$ = lymphocytes of this donor are irradiated
RPMI medium has the following composition:

The composition of RPMI-1640 medium (amounts are in mg/L)
(Literature: MOORE, G.E. et al., J.Am. Med. Assoc. 199, 519 (1967))

| NaCl | 6,000 |
|---|---|
| Na$_2$HPO$_4$7H$_2$O | 1,512 |
| MgSO$_4$7H$_2$O | 100 |
| Ca(NO$_3$)$_2$4H$_2$O | 100 |
| D-glucose | 2,000 |
| Phenol red | 5 |
| NaHCO$_3$ | 2,000 |
| L-arginine | 200 |
| L-asparagine | 50 |
| L-aspartic acid | 20 |
| L-cystine | 50 |
| L-glutamine | 300 |
| L-glutamic acid | 20 |
| Glycine | 10 |
| L-histidine | 15 |
| L-hydroxyproline | 20 |
| L-isoleucine | 50 |
| L-lysine HCl | 40 |
| L-methionine | 15 |
| L-phenylalanine | 15 |

Table 9-continued

| L-proline | 20 |
|---|---|
| L-serine | 30 |
| L-threonine | 20 |
| L-tryptophan | 5 |
| L-tyrosine | 20 |
| L-valine | 20 |
| Glutathione | 1 |
| Biotin | 0.2 |
| Vitamine B$_{12}$ | |
| D-Ca pantothenate | 0.25 |
| Choline chloride | 3 |
| Folic acid | 1 |
| i-Insoitol | 35 |
| Nicotinamide | 1 |
| p-Aminobenzoic acid | 1 |
| Pyridoxine HCl | 1 |
| Riboflavin | 0.2 |
| Thiamine HCl | 1 |

What is claimed is:

1. Activated MASF comprising the factor MASF, activated by from 0.1 to 50 mM of a mercapto compound of the formula

wherein
R is hydrogen or methyl,
X is hydroxyl or amino and
Y is hydrogen, carboxyl or alkyl having 1 to 6 carbon atoms unsubstituted or substituted by hydroxyl, mercapto or hydroxyl and mercapto said mercapto compound being added in a concentration of from 0.01 to 50 mM.

2. Activated MASF according to claim 1, in the form of whole foetal calf serum activated by a said mercapto compound of formula I as defined hereinbefore.

3. Activated MASF according to claim 1, in the form of an MASF-containing blood serum fraction activated by a said compound of the formula I.

4. Activated MASF according to claim 3, wherein the blood serum fraction is obtained from human, murine, rat, rabbit or cattle blood serum.

5. Activated MASF according to claim 1, wherein the compound of the formula (I) is mercaptoethanol.

6. Activated MASF according to claim 1, wherein the MASF has a molecular weight of the order of 50,000.

7. Activated MASF according to claim 1, wherein the MASF is precipitable by ammonium sulphate at a concentration of from 33 to 55% of saturation.

8. A pharmaceutical composition containing as an active ingredient an immunoregulatory effective amount of activated MASF according to claim 1 in admixture with a solid or liquefied gaseous diluent or in admixture with a liquid diluent other than a solvent of a molecular weight less than 200 except in the presence of a surface-active agent.

9. A pharmaceutical composition containing as an active ingredient an immunoregulatory effective amount of activated MASF according to claim 1 in the form of a sterile and/or isotonic aqueous solution.

10. A medicament in dosage unit form comprising an immunoregulatory effective amount of activated MASF according to claim 1 together with an inert pharmaceutical carrier.

11. A medicament of claim 10 in the form of ampoules.

12. A method of combating disorders of the macrophage function, disorders of the lymphocyte T-cell function, induced immunodeficiencies, or anergic conditions in warm-blooded animals which comprises administering to the said animals an immunoregulatory effective amount of activated MASF according to claim 1 either alone or in admixture with a diluent or in the form of a unit-dosage form medicament.

13. A method of immunoregulation in warm-blooded animals which comprises administering to the said animals an immunoregulatory amount of activated MASF according to claim 1 either alone or in admixture with a diluent or in the form of a unit-dosage form medicament.

14. An activated MASF of claim 1 wherein the concentration of the mercapto compound is 1 to 20 mM.

15. Process for the preparation of activated MASF which comprises reacting MASF, as defined hereinbefore, with at least one mercapto compound of the formula

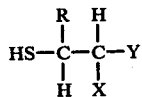 (I)

wherein
R is hydrogen or methyl,
X is hydroxyl or amino and
Y is hydrogen, carboxyl or alkyl having 1 to 6 carbon atoms unsubstituted or substituted by hydroxyl, mercapto or hydroxyl and mercapto, said mercapto compound being added in a concentration of from 0.01 to 50 mM.

16. A process according to claim 15 wherein whole foetal calf serum is reacted with at least one compound of formula I.

17. A process according to claim 15 wherein an MASF-containing blood serum fraction obtained from whole blood serum is reacted with at least one compound of formula I.

18. A process according to claim 17 which includes the preliminary step of fractionating whole blood serum so as to produce said MASF containing blood serum fraction.

19. A process according to claim 15 wherein whole blood serum is reacted with at least one compound of formula I and the resulting activated-MASF containing serum is fractionated so as to produce an activated-MASF containing blood serum fraction.

20. A process according to claim 18 wherein fractionating is effected by means of one or more chromatographic and/or precipitation steps.

21. A process according to claim 20 wherein fractionating comprises ultrafiltration so as to exclude material having a higher or lower molecular weight than does MASF or activated MASF.

22. A process according to claim 20 wherein fractional precipitation using ammonium sulphate or polyethylene glycol is employed.

23. A process according to claim 20 wherein exclusion or ion-exchange chromatography is used for fractionating.

24. A process according to claim 17 wherein the whole blood serum is human, murine, rat, rabbit or cattle whole blood serum.

25. A process according to claim 15 wherein the at least one compound of formula I is mercaptoethanol.

26. A process according to claim 15 wherein when the activated MASF is obtained in the form of a solution or suspension containing the activated MASF, said solution or suspension is concentrated.

27. A process according to claim 26 wherein concentration is effected by means of precipitation by the addition of an alcohol or a ketone; by lyophilization; by molecular sieve filtration or by a combination of said procedures.

* * * * *

UNITED STATES PATENT AND TRADEMARK OFFICE
CERTIFICATE OF CORRECTION

PATENT NO. : 4,159,320
DATED : June 26, 1979
INVENTOR(S) : Hans-Georg Opitz

It is certified that error appears in the above-identified patent and that said Letters Patent are hereby corrected as shown below:

Column 10, line 56, "1.740" should be --1,740--.
Column 11, line 8, insert --$10^5 L_{1210}$FIO-    -- after "sythesis/"; and insert -- * -- after "(cpm)" .
Column 13, line 47,48, delete "50" and "Lokucine 50".
Column 13, line 53 insert "KCL" and "400".
Column 13, line 65, insert "L-leucine" and "50" under "L-isoleucine".
Column 14, line 9, "Vitamine" should be --Vitamin--.
Column 15, line 5 "unction" should be --function--.

Signed and Sealed this

Twentieth Day of November 1979

[SEAL]

Attest:

RUTH C. MASON
Attesting Officer

LUTRELLE F. PARKER
Acting Commissioner of Patents and Trademarks